(12) United States Patent
Lee et al.

(10) Patent No.: US 8,691,882 B2
(45) Date of Patent: Apr. 8, 2014

(54) ORGANIC-INORGANIC HYBRID SCAFFOLDS WITH SURFACE-IMMOBILIZED NANO-HYDROXYAPATITE AND PREPARATION METHOD THEREOF

(75) Inventors: Sang Cheon Lee, Suwon-si (KR); Jeong Ho Chang, Gwangmyeong-si (KR); Jin Hyung Lee, Hwaseong-si (KR); Kyung Ja Kim, Gunpo-si (KR); Sung Eun Kim, Seoul (KR); Ho Chan Hwang, Seoul (KR); Ke-Won Kang, Daejeon (KR); Seog-Jin Seo, Daejeon (KR); Jin-Young Kim, Cheonan-si (KR)

(73) Assignee: Korea Institute of Ceramic Engineering & Technology, Seoul (KR)

( * ) Notice: Subject to any disclaimer, the term of this patent is extended or adjusted under 35 U.S.C. 154(b) by 634 days.

(21) Appl. No.: 12/635,615

(22) Filed: Dec. 10, 2009

(65) Prior Publication Data
US 2010/0160467 A1 Jun. 24, 2010

Related U.S. Application Data

(63) Continuation of application No. PCT/KR2008/006349, filed on Oct. 28, 2008.

(30) Foreign Application Priority Data

Nov. 20, 2007 (KR) .................. 10-2007-0118713

(51) Int. Cl.
*C07K 14/78* (2006.01)
*C08J 9/00* (2006.01)
*C08G 63/06* (2006.01)

(52) U.S. Cl.
USPC ............... 521/50; 521/182; 521/183; 525/50; 525/55; 525/415; 525/420; 525/450; 525/461; 525/538

(58) Field of Classification Search
USPC ........ 521/50, 182, 183; 525/50, 55, 450, 461, 525/538
See application file for complete search history.

(56) References Cited

U.S. PATENT DOCUMENTS

| 6,165,486 A | 12/2000 | Marra et al. |
| 2007/0254007 A1 | 11/2007 | Bumgardner et al. |

FOREIGN PATENT DOCUMENTS

| JP | 2001172511 A | * | 6/2001 |
| KR | 10-0482439 | | 4/2005 |
| KR | 1020050054349 A | | 6/2005 |
| KR | 100500534 B1 | | 7/2005 |
| KR | 100845560 B1 | | 7/2008 |

OTHER PUBLICATIONS

Lee, Sang Cheon, et al., In-situ synthesis of reactive hydroxyapatite nano-crystals for a novel approach of surface grafting polymerization, Journal of Materials Chemistry, 2007, vol. 17, issue 2, pp. 174-180.
International Search Report from PCT/KR2008/006349.
Written Opinion issued during the international phase of PCT/KR2008/006349.

* cited by examiner

*Primary Examiner* — Irina S Zemel
(74) *Attorney, Agent, or Firm* — Knobbe, Martens, Olson & Bear, LLP

(57) ABSTRACT

Provided are an organic-inorganic hybrid scaffold with surface-immobilized nano-hydroxyapatite, and a method for the fabrication thereof. The scaffold is fabricated by reacting an acid group present on a surface of nano-hydroxyapatite with a primary amine present on a surface of a polymer support in the presence of EDC (1-ethyl-3-dimethylaminopropyl carbodiimide) to immobilize nano-hydroxyapatite onto the surface of the polymer support. The surface of nano-hydroxyapatite is previously grafted with poly(ethylene glycol methacrylate phosphate) (PolyEGMP) having phosphonic acid functionality or with a polymer having carboxylic acid functionality.

9 Claims, 4 Drawing Sheets

ORGANIC-INORGANIC HYBRID SCAFFOLDS WITH SURFACE-IMMOBILIZED NANO-HYDROXYAPATITE AND PREPARATION METHOD THEREOF

CROSS REFERENCE TO RELATED APPLICATIONS

This application is a continuation application under 35 U.S.C. §365(c) of International Application No. PCT/KR2008/006349, filed Oct. 28, 2008 designating the United States. International Application No. PCT/KR2008/006349was published in English as WO2009/066879 A2 on May 28, 2009. This application further claims the benefit of the earlier filing date under 35 U.S.C. §365(b) of Korean Patent Application No. 10-2007-0118713 filed Nov. 20, 2007. This application incorporates herein by reference the International Application No. PCT/KR2008/006349 including the International Publication No. WO2009/066879 A2 and the Korean Patent Application No. 10-2007-0118713 in their entirety.

TECHNICAL FIELD

The present invention relates to organic-inorganic scaffold with nano-hydroxyapatite immobilized to the surface thereof and a method for the fabrication thereof.

BACKGROUND ART

Combinations of nano-hydroxyapatite ($Ca_{10}(PO_4)_6(OH)_2$) and biopolymers, known to provide ideal environments for effective bone regeneration, are hybrid scaffolds attractive to the bone tissue engineering. The spontaneous bone structure is a hybrid structure of the inorganic nano-hydroxyapatite and the organic extracellular matrix (ECM) in which collagens give structural support to resident cells. Three-dimensional porous scaffolds play not only an important role in activating osteoblast cells, but also provide temporary bone structures for defective portions. One of the most important factors with which effective bone regeneration materials are designed is to alter the surface properties of the porous scaffold so as for cells to effectively adhere to, migrate on and proliferate at the scaffold. Hence, the surface functionalization of porous scaffolds with highly bioactive nano-hydroxyapatite is one of the ideal approaches to achieve effective hybrid nano-scaffolds applicable to bone regeneration.

DISCLOSURE

Technical Problem

To date, almost all methods of preparing three-dimensional hybrid scaffolds are based on the simple physical mixing of polymers and nanohydroxyapatite. However, these conventional methods are difficult to apply to the exposure of nano-hydroxyapatite at a nano level on porous scaffold surfaces. For this reason, limitations are imparted to the expression of the intrinsic physical properties of nanohydroxyapatite, such as protein absorption and mineral induction, which leads to an improvement in cell adhesion to the surface of the biomaterial.

Generally, in order to provide a highly cytotropic environment for the surface thereof, a biopolymer is mixed with the inorganic nano-hydroxyapatite. In this regard, first, a solution must be suggested to the problem of the inherent low affinity between the surface of nano-hydroxyapatite and the surface of the polymer. Due to the low surface reactivity of nano-hydroxyapatite, it cannot be stably immobilized to the surface of the biopolymer via chemical bonds or physical adhesion. In addition, nano-hydroxyapatite highly tends to aggregate into precipitates due to the high density thereof (3.2 g/mL) as well as to intermolecular van der Waals interaction and hydrogen bonds. These two inherent properties of nano-hydroxyapatite make it impossible to stably immobilize hydroxyapatite at a nano level onto the surface of the polymer support.

Therefore, if it shows high colloidal stability in solutions, dispersibility at a nano level and high surface reactivity, nano-hydroxyapatite is thought to be stably immobilized to the surface of polymer scaffolds.

Technical Solution

Leading to the present invention, intensive and thorough research into a scaffold suitable for use in bone tissue engineering, conducted by the present inventors, resulted in the finding that when surface-modified nano-hydroxyapatite, showing excellent dispersibility and surface reactivity, was immobilized onto the surface of a polymer support through a chemical bond, the resulting organic-inorganic hybrid scaffold can promote the cell adhesion and growth therein and increase alkaline phosphatase (ALP) activity, thus providing environments very suitable for the osteogenic differentiation of human adipose-derived stem cells and the growth of osteoblasts.

BEST MODE

Figure 1:
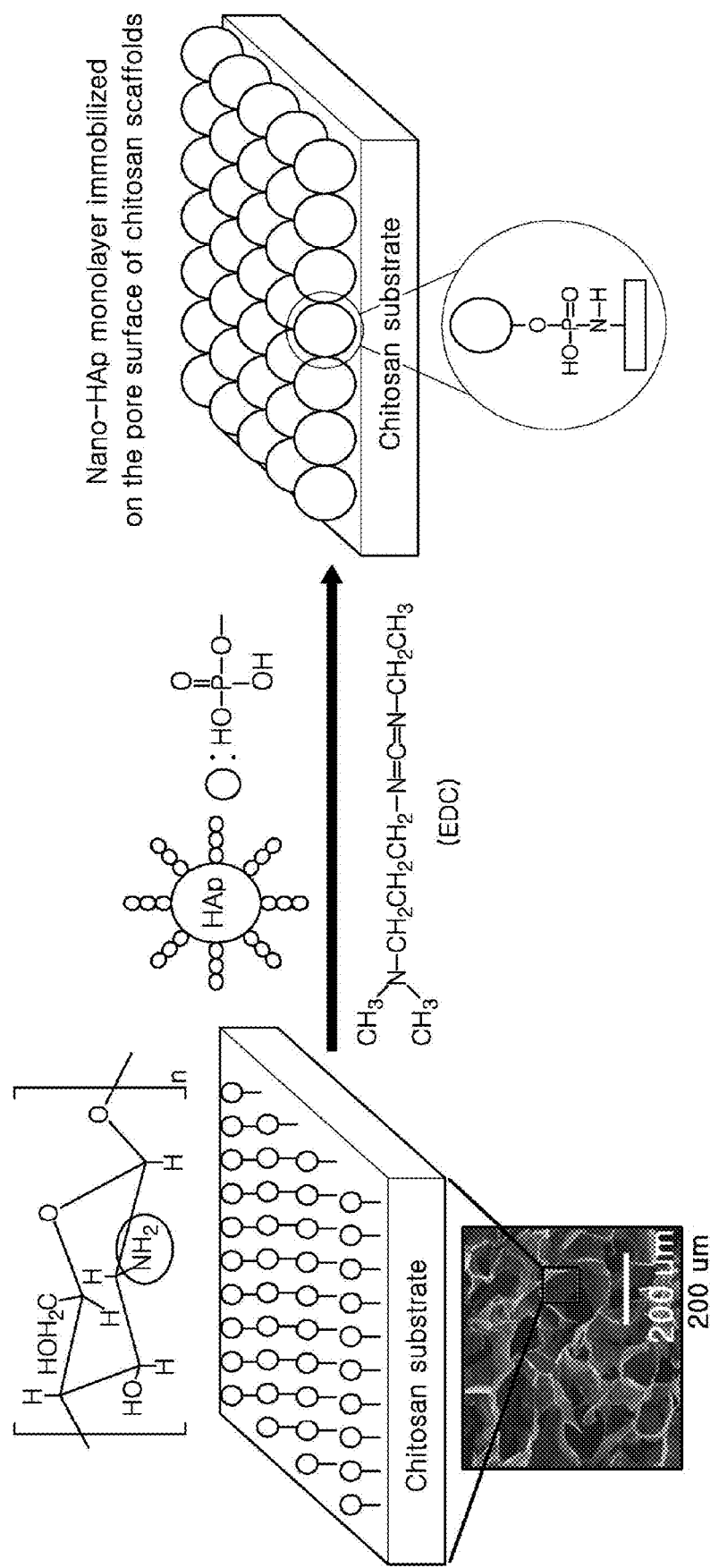
FIG. 1 is a view showing the mechanism of immobilizing surface-modified nano-hydroxyapatite onto the surface of porous chitosan support.

In accordance with an aspect thereof, the present invention provides an organic-inorganic hybrid scaffold with nano-hydroxyapatite immobilized to the surface thereof.

MODE FOR INVENTION

In accordance with another aspect thereof, the present invention provides a method for preparing the organic-inorganic hybrid scaffold, comprising reacting an acid group present on a surface of nano-hydroxyapatite with a primary amine present on a surface of a polymer support in the presence of EDC (1-ethyl-3-dimethylaminopropyl carbodiimide) to immobilize nano-hydroxyapatite onto the surface of the polymer support, the surface of nano-hydroxyapatite being grafted with poly[(ethylene glycol methacrylate phosphate);

(PolyEGMP)] having phosphonic acid functionality or with a polymer having carboxylic acid functionality.

For use in the organic-inorganic hybrid scaffold of the present invention, nano-hydroxyapatite ranges in size from 5 to 300 nm and preferably has a surface dimension of 120 nm×20 nm which is modified with a PolyEGMP graft having phosphonic acid functionality. At this time, PolyEGMP is grafted in an amount of 16 wt % to the surface of nano-hydroxyapatite (Korean Patent Application No. 10-2007-9573 and Journal of Materials Chemistry, 2007, 17. 174-180). Instead of PolyEGMP with phosphonic acid functionality, a polymer with carboxylic acid functionality may be used to modify the surface of nano-hydroxyapatite. Examples of the polymer with carboxylic acid functionality useful in the present invention include poly(acrylic acid), poly(methacrylic acid), poly(aspartic acid), poly(glutamic acid, alginic acid and hyaluronic acid). Grafted with phosphonic acid or carboxylic acid, the surface-modified nano-hydroxyapatite of the present invention shows excellent stability of colloidal dispersions (zeta potential=−22~31 mv) and high surface reactivity. It crystallizes in a needle-like form.

Examples of the polymer support suitable for use in the organic-inorganic hybrid scaffold of the present invention according to the present invention include poly(L-lactide), poly(D-lactide), poly(DL-lactide), poly(glycolic-co-lactic acid), poly(ε-caprolactone), polycarbonate, chitosan, alginate, hyaluronic acid, dextran, starch, methylcellulose, gelatin, collagen, polyanhydride, poly(ortho esters), polyphosphazene, and combinations thereof, but are not limited thereto. The polymer support may be of a dense type, a porous block type, a nano/micro-fiber type, or a microsphere type, but is not limited thereto. When it is of a porous block type, the polymer support preferably ranges in pore size from 50 to 500 μm.

A detailed description is given of the method for the preparation of an organic-inorganic hybrid scaffold in accordance with the present invention, below.

The nano-hydroxyapatite, onto the surface of which poly (ethylene glycol methacrylate phosphate) with phosphonic acid functionality or a polymer with carboxylic acid functionality (PolyEGMP-HAp) is grafted, is prepared using the method disclosed in Korean Patent Application No. 10-2007-9573.

For this, the polymer is dissolved in a 2% acetic acid solution. The resulting aqueous polymer solution is placed in a cylindrical Teflon mold and frozen at −20° C. for 24 hours in a freezer. The frozen solution was freeze-dried for 48 hours. The polymer support is immersed for 24 hours in 1 N sodium hydroxide to neutralize the acetic acid remaining therein, followed by washing with distilled water.

The nano-hydroxyapatite onto the surface of which poly (ethylene glycol methacrylate phosphate) (PolyEGMP) (PolyEGMP-HAp) with phosphonic acid functionality or a polymer with carboxylic acid functionality is grafted is dispersed in combination with the polymer support at various weight ratios in distilled water. The resulting dispersions are made to be uniform by sonication with a bath-type ultrasonicator and their pH values are adjusted to 5.8 with 1 N HCl. The uniform dispersions are reacted with EDC (1-ethyl-3-dimethylaminopropyl carbodiimide) for 48 hours and washed many times with distilled water. Freeze-drying for 48 hours allows the dispersions to afford organic-inorganic hybrid scaffolds (SI-Hybrid) with nano-hydroxyapatite immobilized to the surface thereof.

An observation through SEM (scanning electron microscopy) and XPS (X-ray photoelectron spectroscopy) shows that nano-hydroxyapatite is successfully immobilized to the surface of the organic-inorganic hybrid scaffolds (FIG. 2C) and is formed as a nanometers-thick monolayer structure. Also, XPS data indicate that the component elements (Ca and P) of nano-hydroxyapatite are detected from the organic-inorganic hybrid scaffolds of present invention (FIG. 2F), with the presence of Ca in an amount of 8.4% on the surface of the scaffolds. Also, the nano-hydroxyapatite immobilized to the surface of the polymer support is found to amount to 1~50 wt % and preferably to 6~24 wt % on the basis of the total weight of the scaffold as measured by a thermogravimetric analyzer.

With ability to allow cell adhesion thereto and cell growth and to increase alkaline phosphatase (ALP) activity, the organic-inorganic hybrid scaffold with nano-hydroxyapatite immobilized to the surface thereof in accordance with the present invention can provide an environment suitable for the differentiation of human adipose-derived stem cells into osteoblasts and the growth of osteoblasts.

Therefore, the method for preparing the organic-inorganic hybrid scaffold with nano-hydroxyapatite immobilized to the surface thereof in accordance with the present invention can be applied for the development of various shapes and sizes of functional, biocompatible scaffolds having cytotropic surface.

A better understanding of the present invention may be obtained through the following examples which are set forth to illustrate, but are not to be construed as limiting the present invention.

PREPARATION EXAMPLE 1

Preparation of Nano-Hydroxyapatite Having Surface Modified with Poly(ethylene glycol methacrylate phosphate) (PolyEGMP-HAp)

1. Preparation of Nano-Hydroxyapatite Having Thiol Groups Introduced onto the Surface Thereof (HAp-SH)

Nano-hydroxyapatite with thiol groups introduced to the surface thereof was prepared using a hydrothermal method. 0.25 M of calcium hydroxide ($Ca(OH)_2$) was uniformly dissolved at 60° C. in 600 mL of distilled water. To 300 mL of distilled water were simultaneously added 0.3 M of phosphoric acid ($H_3PO_4$) and 0.047 M of 3-mercaptopropionic acid ($HSCH_2CH_2CO_2H$) followed by mixing. The homogenous mixture was dropwise added at a rate of 1 mL per min to the aqueous calcium hydroxide solution. Afterwards, the pH of the resulting reaction mixture was adjusted to 7 with 0.1 N NaOH. The neutralized mixture was washed five times with distilled water by centrifugation at a speed of 2500 rpm for 20 min. Thereafter, freeze-drying for 48 hours results in nano-hydroxyapatite with thiol groups introduced onto the surface thereof (HAp-SH).

2. Grafting of PolyEGMP onto Surface of Hydroxyapatite [PolyEGMP-HAp]

To 50 mL of N,N-dimethylformamide (DMF) was added 2.5 g of the nano-hydroxyapatite the surface of which thiol groups (SH) were introduced as prepared in Example 1, followed by ultrasonication for 30 min in a bath-type ultrasonicator. The solution thus homogeneously dispersed was bubbled for 30 min with nitrogen gas to remove oxygen gas therefrom. One gram of ethylene glycol methacrylate phosphate (EGMP) was added, together with 0.02 g of the initiator 2,2'-azobisisobutyronitrile (AIBN), to the solution, followed by reaction at 60° C. for 18 hours in a nitrogen atmosphere. Subsequently, the reaction mixture was washed five times with 1 M sodium hydroxide by centrifugation at a speed of 3000 rpm for min. Finally, poly(ethylene glycol methacrylate phosphate) (PolyEGMP)-grafted nano-hydroxyapatite (PolyEGMP-HAp) was obtained after freeze-drying for 48 hours.

PREPPARATION EXAMPLE 2

Preparation of Porous Chitosan Support

An aqueous chitosan solution (3 wt %) was prepared with a 2% acetic acid solution (10 mL). The chitosan solution was placed in a cylindrical Teflon mold (diameter: 13 mm, thickness: 12 mm) and frozen at −20° C. for 24 hours in a freezer to afford a cylindrical chitosan support, having a size of 12×3 mm, for cell culture. This chitosan support was immersed for 24 hours in 1 N sodium hydroxide to neutralize remaining acetic acid, and washed with distilled water.

EXAMPLE 1

Preparation of Porous Chitosan Scaffold with Nano-Hydroxyapatite Immobilized to the Surface Thereof [SI-Hybrid]

Mixtures of the surface-modified nano-hydroxyapatite prepared in Preparation Example 1 and the porous chitosan support prepared in Preparation Example 2 at various weight: ratios (10:0, 7:3, 3:7) were dispersed in distilled water (2 mL). The dispersions were sonicated for 30 min in a bath-type ultrasonicator and the pH values of the resulting homogeneous dispersions were adjusted into 5.8. To the homogeneous dispersions was added EDC (1-ethyl-3-dimethylaminopropyl carbodiimide). After reaction for 48 hours, the resulting supports were washed many times with distilled water. Freeze-drying for 48 hours afforded porous chitosan scaffolds with nano-hydroxyapatite immobilized to the surface thereof (SI-Hybrid).

The mechanism of immobilizing the surface-modified nano-hydroxyapatite onto the surface of porous chitosan is illustrated in FIG. 1.

COMPARATIVE EXAMPLE 1

Fabrication of Bulk Phase-Mixed Chitosan/Nano-Hydroxyapatite Composite Scaffolds [BM-Hybrid]

An aqueous 3 wt % chitosan solution was prepared in a 2% acetic acid solution (10 mL). To the homogeneous chitosan solution was added 24 wt % (or 6 wt %) of nano-hydroxyapatite (0.095 g). The resulting chitosan/nano-hydroxyapatite solution was placed in a cylindrical Teflon mold (diameter: 13 mm, thickness: 12 mm) and frozen at −20° C. for 24 hours in a freezer. Freeze-drying for 3 days afforded bulk phase-mixed porous chitosan scaffold (BM-Hybrid).

COMPARATIVE EXAMPLE 2

Fabrication of Bulk Phase-Mixed Chitosan/Surface-Modified Nano-Hydroxyapatite Composite Scaffolds Bulk phase-mixed chitosan/surface-modified nano-hydroxyapatite composite scaffolds were fabricated in the same manner as in Comparative Example 1, with the exception that the surface-modified nano-hydroxyapatite prepared in Preparation Example 1 was used instead of nano-hydroxyapatite.

EXPERIMENTAL EXAMPLE 1

Physical Properties of Porous Chitosan Scaffolds with Surface-Immobilized Nano-Hydroxyapatite The porous chitosan scaffolds with surface-immobilized nano-hydroxyapatite were analyzed for surface structure and surface element composition through scanning electron microscopy (SEM) and X-ray photoelectron spectroscopy (XPS), respectively. Also, the porous scaffolds were quantified for nano-hydroxyapatite by thermogravimetric analysis (TGA).

Figure 2:
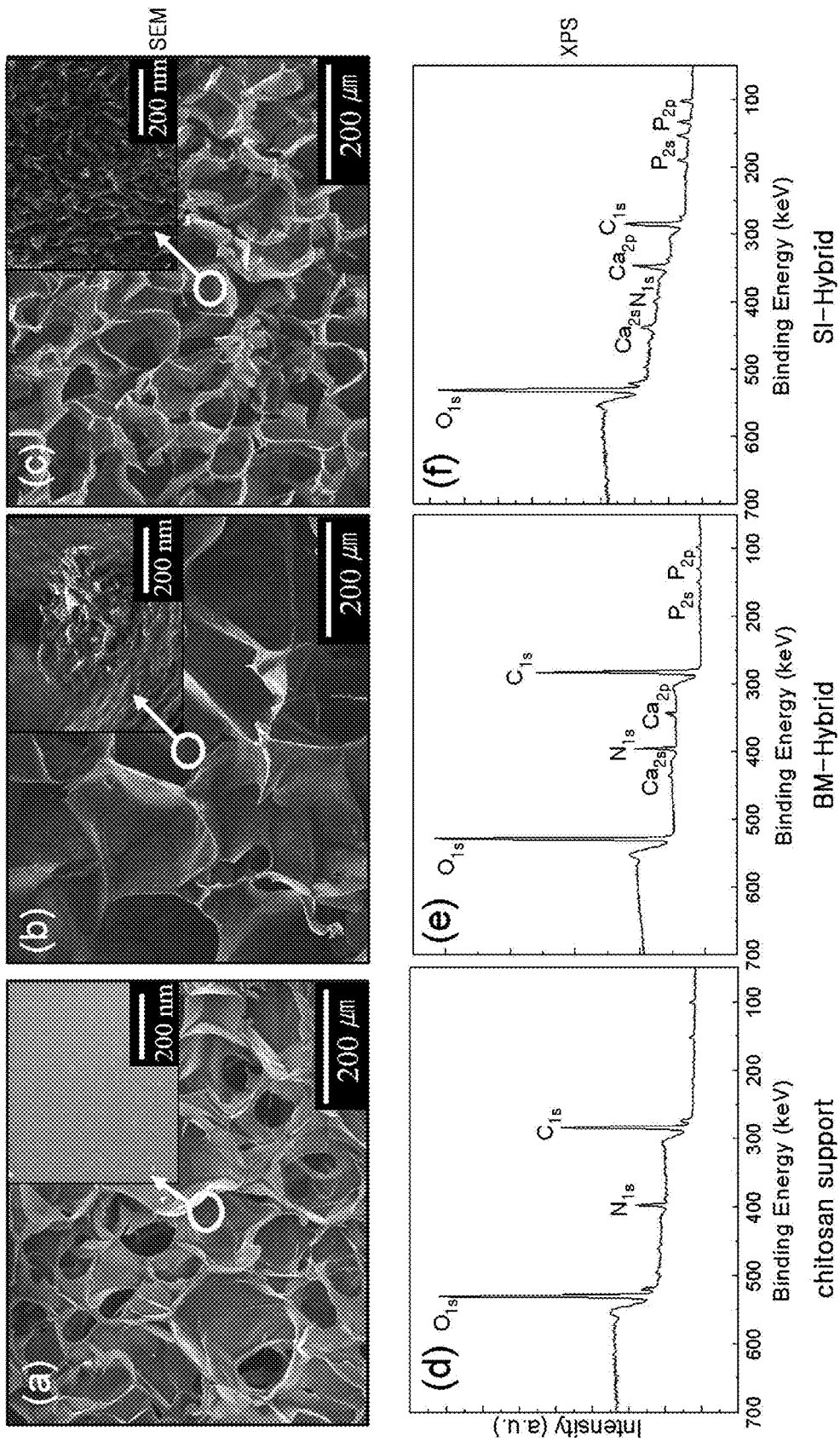
FIG. 2 shows surface and element structures of porous chitosan scaffolds with surface-immobilized nano-hydroxyapatite and other chitosan scaffolds through SEM (scanning electron microscopy) and XPS (X-ray photoelectron spectroscopy) [SEM—(a) chitosan support, (b) BM-Hybrid, (c) SI-Hybrid; XPS—(d) chitosan support, (e) BM-Hybrid, (f) SI-Hybrid].

Results of the SEM and the XPS are given in FIG. 2 [SEM—chitosan scaffold (a), BM-Hybrid (b) and SI-Hybrid (c); XPS—Chitosan scaffold (d), BM-Hybrid (e) and SI-Hybrid (f)].

In the porous chitosan scaffolds with surface-immobilized nano-hydroxyapatite (SI-Hybrid) in accordance with the present invention, as seen in FIG. 2, a needle-like structure of surface-modified nano-hydroxyapatite was successfully immobilized onto the surface of the porous chitosan support (c) and was formed as a nanometers-thick monolayer structure covering the surface. Also, XPS detected the component elements (Ca and P) of nano-hydroxyapatite on the surface of the porous chitosan scaffolds with surface-immobilized nano-hydroxyapatite (SI-Hybrid) (f), with Ca present in an amount of 8.4%, confirming that the nano-hydroxyapatite was exposed on the chitosan support. In contrast, SEM failed to show the exposure of nano-hydroxyapatite on the surface of BM-hybrid, but demonstrated that nano-hydroxyapatite was hidden in the chitosan (b). Further, a smaller Ca ion peak was read in the XPS of BM-Hybrid than in that of SI-Hybrid, and the Ca element present on the surface of BM-Hybrid was measured to be only 0.8%.

In addition, the amount of the nano-hydroxyapatite immobilized on the surface of the porous chisotan scaffold of the present invention could be easily determined by adjusting the feed amount of the surface-modified nano-hydroxyapatite, and was found to be with the range of from 6 to 24 wt % as measured by TGA.

EXPERIMENTAL EXAMPLE 2

Assay for Cell Proliferation in Porous Chitosan Scaffold with Surface-Immobilized Nano-hydroxyapatite (MTT Assay)

An MTT assay was used to quantitatively analyze the porous chitosan scaffold with surface-immobilized nano-hydroxyapatite according to the present invention for ability to proliferate cells. To this end, first, a culture medium containing NIH3T3 fibroblasts ($5 \times 10^5$ cells/mL) was loaded on the porous chitosan scaffolds fabricated in Preparation Example 2, Example 1, and Comparative Examples 1 and 2, followed by incubation for 7 days (n=3). The porous chitosan scaffolds were washed three times with PBS (phosphate buffered saline). 20 µl of an MTT [3-(4,5-dimethylthiazol-2-yl)-2,5-diphenyl tetrazolium bromide] solution (phenol red-free RPMI-1640 containing 5 mg/mL MTT) and 500 µl of DMEM (Dulbecco's modified Ealge's medium) were added to each scaffold before incubation at 37° C. for 4 hours. The formazan precipitates thus formed were dissolved in DMSO (500 µl) and the solutions were aliquoted in an amount of 200 µl per well to 96-well plates which were then read for absorbance at 570 nm in a microplate reader (Spectra Max 250, Molecular Devices, Sunnyvale, Calif.).

Figure 3:
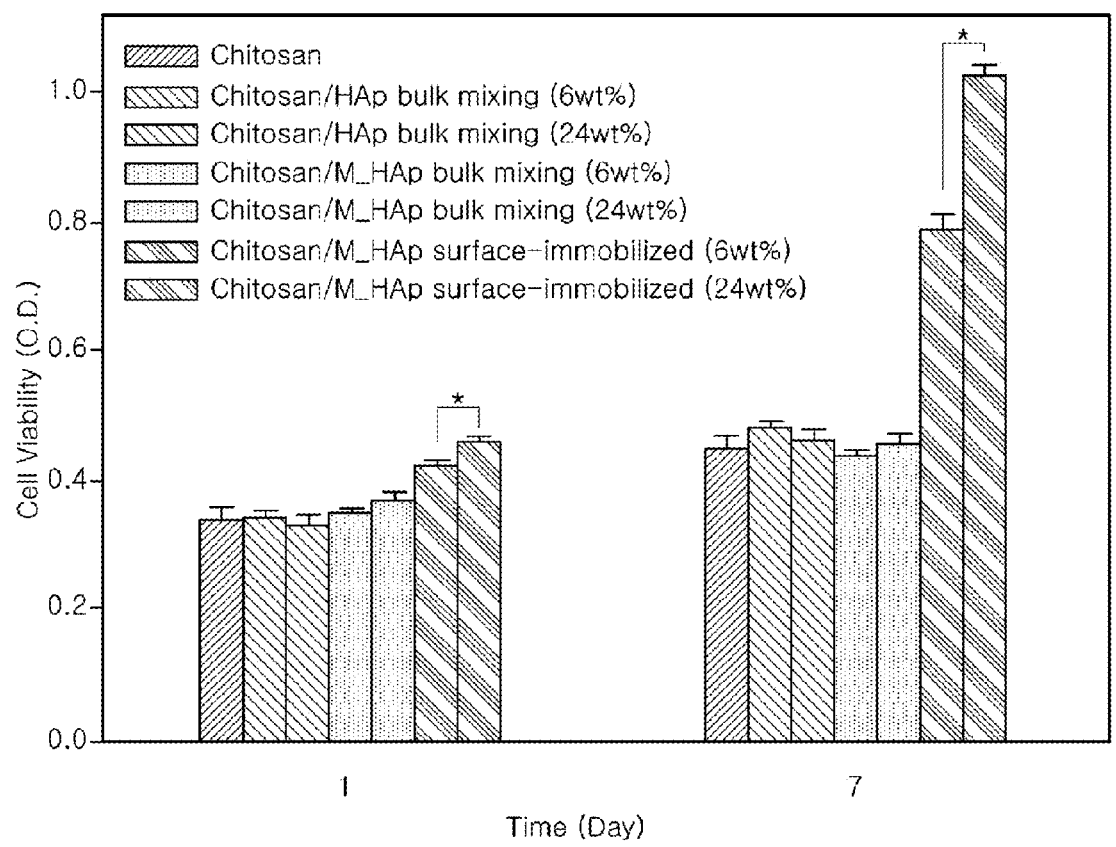
FIG. 3 is a histogram showing cell proliferation in porous chitosan scaffolds with surface-immobilized nano-hydroxyapatite and other chitosan scaffolds as measured by MTT assay.

The results are shown in FIG. 3.

As seen in FIG. 3, the chitosan scaffolds with surface-immobilized nano-hydroxyapatite were found to allow the cells to grow more actively than the control chitosan scaffold (black bars) and to increase cell proliferation with time. The bulk phase-mixed chitosan scaffolds (BM-Hybrid) II (green bars) and III (red bars) fabricated in Comparative Examples 1 and 2 could not provide such a sufficient surface affinity as to effectively grow the cells. This is thought to be attributed to the fact that the bulk process cannot ensure the positioning of nano-hydroxyapatite as precisely as at a nano level on the surface of the porous chitosan support. In addition, a significant increase in cell adhesion and growth was found on the chitosan scaffolds with surface-immobilized nano-hydroxyapatite (SI-hybrid IV, yellow bars) as compared to the chitosan scaffold controls. During the incubation for 7 days, the cells counts had been increased two- or more folds in the porous chitosan scaffold IV (SI-Hybrid) of the present invention as compared to the bulk phased-mixed chitosan scaffold II (green bar) and III (red bar) (BM-Hybrid). Further, the cells were found to further adhere to and grow on SI-Hybrid as the amount of the surface-grafted nano-hydroxyapatite increased from 6 to 24 wt %.

EXPERIMENTAL EXAMPLE 3

Assay for Alkaline Phosphatase Activity of Porous Chitosan Scaffold with Surface-Immobilized Nano-Hydroxyapatite In order to evaluate the osteogenic differentiation of human adipose-derived stem cells into osteoblasts in the porous chitosan scaffold with surface-immobilized nano-hydroxyapatite, cell-scaffold structures were measured for alkaline phosphatase (ALP) activity.

After being provided for growing human adipose-derived stem cells for 1 and 5 weeks, the porous scaffolds fabricated in Preparation Example 2, Example 1 and Comparative Examples 1 and 2 were fixed with 10% paraformaldehyde and washed with PBS. The cells were disrupted for 2 min with 2 mL of a lysis buffer solution (0.02% Triton X-100, Sigma). The cell lysates were centrifuged at 14,000 rpm for 15 min. After being removed, 6 μl of each of the supernatants thus formed was mixed with 54 μl of a 0.02% cell lysis buffer prepared by mixing 100 μl of 1 M Tris-HCl (Sigma, pH 9.0), 200 μl of 5 mM $MgCl_2$ and 20 μl of 5 mM para-nitrophenyl-2-phosphate (PNPP, Sigma) and incubated at 37° C. for 30 min. The enzyme reaction was terminated with 1 N NaOH. Para-nitrophenol levels, which indirectly exhibit the activity of alkaline phosphatase, were measured for their absorbance at 405 nm read in a microplate reader. The results are expressed as units/min/mg protein/scaffold.

Figure 4:
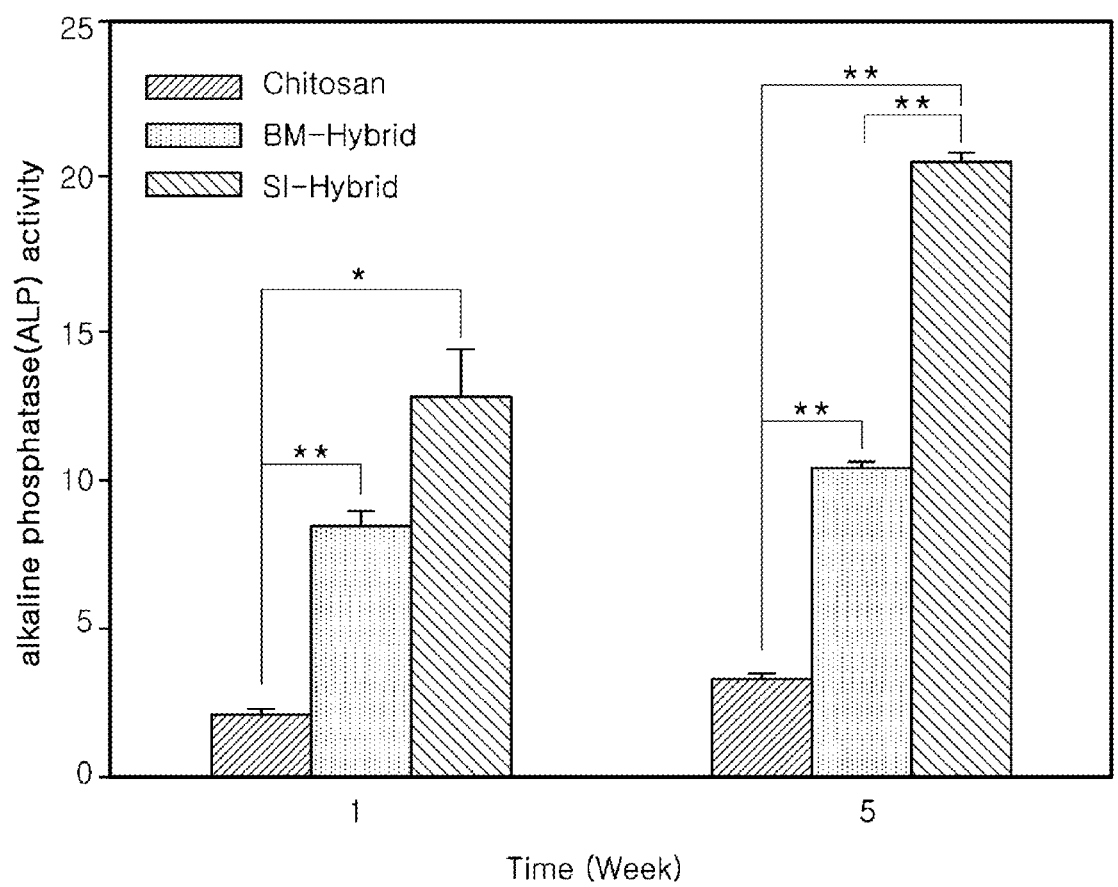
FIG. 4 is a histogram showing alkaline phosphatase (ALP) activity in porous chitosan scaffolds with surface-immobilized nano-hydroxyapatite and other chitosan scaffolds.

The results are shown in FIG. 4.

As seen in FIG. 4, the human adipose-derived stem cells were found to remarkably differentiate in SI-Hybrid during the incubation for five weeks. It was also observed that SI-Hybrid showed a more active osteogenic differentiation behavior than did the control chitosan scaffold and BM-Hybrid. The alkaline phosphatase activity on SI-Hybrid was measured to be higher than that on the control chitosan or BM-Hybrid after incubation for one week (*P<0.05) and the difference of alkaline phosphatase activity between the SI-Hybrid and the control or BM-Hybrid was further expanded (**P<0.01).

Industrial Applicability

As described hitherto, the organic-inorganic hybrid scaffold with nano-hydroxyapatite immobilized to the surface thereof in accordance with the present invention can promote the cell adhesion and growth therein and increase alkaline phosphatase (ALP) activity, thus providing environments very suitable for the osteogenic differentiation of human adipose-derived stem cells and the growth of osteoblasts. Therefore, the method for fabricating an organic-inorganic hybrid scaffold with surface-immobilized nano-hydroxyapatite in accordance with the present invention can find an application in the development of functional, biocompatible scaffolds with cytotropic surfaces in various shapes and sizes.

The invention claimed is:

1. An organic-inorganic hybrid scaffold comprising:
   a chitosan comprising primary amine terminals; and
   a nano-hydroxyapatite particle immobilized to the chitosan via a polymeric link linking between the chitosan and the nano-hyproxyapatite particle,
   wherein the nano-hydroxyapatite particle comprises a polymeric moiety grafted onto a surface thereof, wherein the grafted polymeric moiety comprises at least one of a phosphonic acid terminal and a carboxylic acid terminal, and
   wherein the polymeric link comprises a peptide or phosphoramidate bond formed by a reaction in the presence of EDC (1-ethyl-3-dimethylaminopropyl carbodiimide) between one of the primary amine terminals of the chitosan and the carboxylic acid terminal or the phosphonic acid terminal of the grafted polymeric moiety.

2. The organic-inorganic hybrid scaffold according to claim 1, wherein the polymeric moiety comprises at least one selected from the group consisting of poly(ethylene glycol methacrylate phosphate), poly(acrylic acid), poly(methacrylic acid), poly(aspartic acid), poly(glutamic acid), alginic acid, and hyaluronic acid.

3. The organic-inorganic hybrid scaffold according to claim 1, wherein the nano-hydroxyapatite particle ranges in size from 5 to 300 nm.

4. The organic-inorganic hybrid scaffold according to claim 1, wherein the scaffold comprises a plurality of nano-hydroxyapatite particles, and the total weight of the nano-hydroxyapatite particles is in an amount of 1 to 50 wt % based on the total weight of the scaffold.

5. The organic-inorganic hybrid scaffold according to claim 1, wherein the size of the pores ranges from 50 to 500 μm.

6. A method for fabricating the organic-inorganic hybrid scaffold of claim 1, comprising:
   providing a chitosan comprising primary amine terminals;
   providing a nano-hydroxyapatite particle with a polymeric moiety grafted onto a surface thereof, the polymeric moiety comprising at least one terminal selected from the group consisting of a phosphonic acid terminal and a carboxylic acid terminal; and
   causing a reaction, in the presence of EDC (1-ethyl-3-dimethylaminopropyl carbodiimide), between one of the primary amine terminals of the chitosan with the carboxylic acid terminal or the phosphonic acid terminal of the grafted polymeric moiety to form a polymeric link comprising a peptide or phosphoramidate bond, thereby immobilizing the nano-hydroxyapatite particle to the chitosan.

7. The method of claim 6, wherein the polymeric moiety comprises at least one selected from the group consisting of poly(ethylene glycol methacrylate phosphate), poly(acrylic acid), poly(methacrylic acid), poly(aspartic acid), poly(glutamic acid), alginic acid, and hyaluronic acid.

8. The method of claim 6, wherein causing the reaction comprises mixing chitosan and the nano-hydroxyapatite particle in water to form a dispersion at pH 5.8.

9. The method of claim 8, wherein causing the reaction further comprises adding EDC to the dispersion.

* * * * *